United States Patent [19]

Heinemann et al.

[11] Patent Number: 5,234,943

[45] Date of Patent: Aug. 10, 1993

[54] FUNGICIDAL 3-(2-CHLORO-3-TRIFLUOROMETHYL-PHENYL)-4-CYANOPYRROLE

[75] Inventors: Ulrich Heinemann, Leichlingen; Albrecht Marhold, Leverkusen; Stefan Dutzmann, Hilden; Heinz-Wilhelm Dehne, Monheim, all of Fed. Rep. of Germany

[73] Assignee: Bayer Aktiengesellschaft, Leverkusen, Fed. Rep. of Germany

[21] Appl. No.: 931,164

[22] Filed: Aug. 17, 1992

Related U.S. Application Data

[60] Continuation-in-part of Ser. No. 760,040, Sep. 13, 1991, Pat. No. 5,166,395, which is a division of Ser. No. 506,414, Apr. 6, 1990, Pat. No. 5,091,408.

[30] Foreign Application Priority Data

Apr. 13, 1989 [DE] Fed. Rep. of Germany ....... 3912156
Aug. 24, 1991 [DE] Fed. Rep. of Germany ....... 4128132

[51] Int. Cl.$^5$ .................. A01N 43/00; C07D 207/34
[52] U.S. Cl. ..................................... 514/427; 548/561
[58] Field of Search .......................... 548/561; 514/427

[56] References Cited

U.S. PATENT DOCUMENTS 4,572,909 2/1986 Campbell et al. .................. 514/356
5,091,408 2/1992 Wollweber et al. ................ 548/561

FOREIGN PATENT DOCUMENTS 0096142 12/1982 European Pat. Off. .
0433805 12/1990 European Pat. Off. .
2927480 7/1979 Fed. Rep. of Germany .
3601285 1/1986 Fed. Rep. of Germany .

Primary Examiner—Patricia L. Morris
Attorney, Agent, or Firm—Sprung Horn Kramer & Woods

[57] ABSTRACT

Fungicidally active 3-(2-chloro-3-trifluoro-methyl-phenyl)-4-cyanopyrrole of the formula

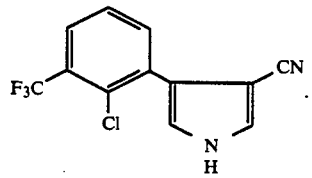

3 Claims, No Drawings

FUNGICIDAL 3-(2-CHLORO-3-TRIFLUOROMETHYLPHENYL)-4-CYANOPYRROLE

This application is a continuation-in-part of application Ser. No. 760,040, filed Sep. 13, 1991, now U.S. Pat. No. 5,166,395, which is a division of application Ser. No. 506,414, filed Apr. 6, 1990, now U.S. Pat. No. 5,091,408.

The invention relates to the new compound 3-(2-chloro-3-trifluoromethylphenyl)-4-cyanopyrrole, to a process for its preparation and to its use as a pesticide, and to new intermediates.

It has been disclosed that certain 3-aryl-4-cyanopyrrole compounds such as, for example, the compound 3-(3-trifluoromethylphenyl)-4-cyanopyrrole have fungicidal properties (cf., for example, EP 96, 142).

However, the activity of these previously known compounds is not entirely satisfactory in all fields of application, in particular when low application rates and concentrations are used.

The new compound 3-(2-chloro-3-trifluoromethylphenyl)-4-cyanopyrrole of the formula (I)

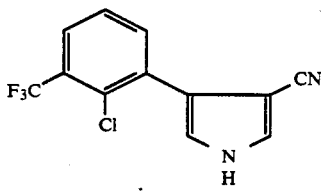

has been found.

Furthermore, it has been found that the new compound 3-(2-chloro-3-trifluoromethylphenyl)-4-cyanopyrrole of the formula (I)

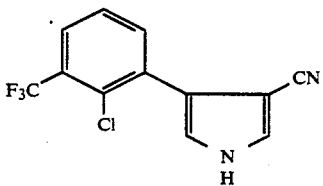

is obtained when 2-chloro-3-trifluoromethylbenzaldehyde of the formula (II)

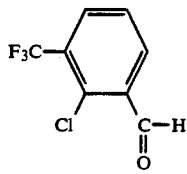

is initially reacted, in a first step, with alkyl cyanoacetates of the formula (III)

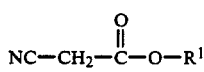

in which
R$^1$ represents alkyl, if appropriate in the presence of a diluent and if appropriate in the presence of a reaction auxiliary, and the resulting α-cyano-cinnamates of the formula (IV)

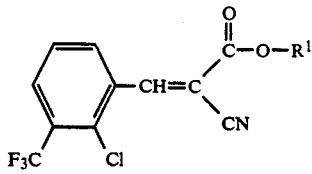

in which
R$^1$ has the abovementioned meaning
are subsequently reacted with p-toluenesulphonylmethyl isocyanide (TOSMIC) of the formula (V)

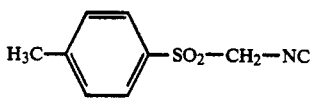

if appropriate in the presence of a diluent and if appropriate in the presence of a reaction auxiliary.

Finally, it has been found that the new compound 3-(2-chloro-3-trifluoromethylphenyl)-4-cyanopyrrole of the formula (I) has a good activity against pests.

Surprisingly, the new compound 3-(2-chloro-3-trifluoromethylphenyl)-4-cyanopyrrole of the formula (I) shows a considerably better fungicidal activity against phytopathogenic fungi than the 3-aryl-4-cyanopyrrole compounds which are known from the prior art such as, for example, the compound 3-(3-trifluoromethylphenyl)-4-cyanopyrrole, which are similar compounds chemically from the point of view of their action.

If, for example, 2-chloro-3-trifluoromethylbenzaldehyde and ethyl cyanoacetate are used as starting compounds, the course of the reaction of the process according to the invention can be represented by the following equation:

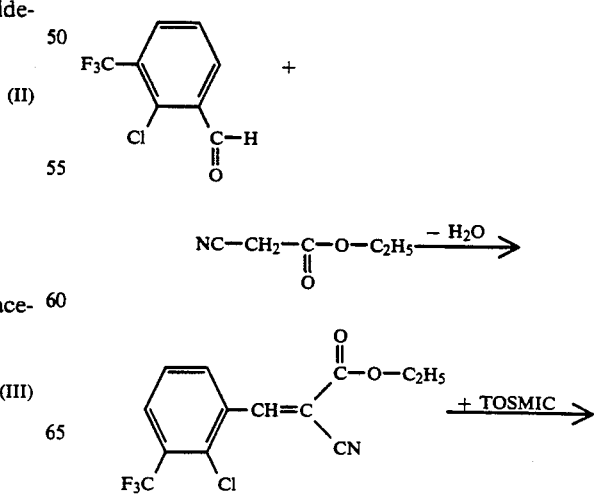

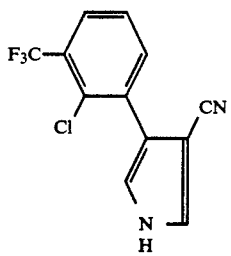

Formula (II) provides a definition of 2-chloro-3-trifluoromethylbenzaldehyde, which is required as a starting compound for carrying out the process according to the invention. 2-Chloro-3-trifluoromethylbenzaldehyde, of the formula (II), has been disclosed (cf., for example, U.S. Pat. No. 4,572,909; EP 145,334; JP 59118782).

Formula (III) provides a general definition of the alkyl cyanoacetates furthermore required as starting substances for carrying out the process according to the invention. In this formula (III), $R^1$ preferably represents straight-chain or branched alkyl having 1 to 6, in particular 1 to 4, carbon atoms. The alkyl cyanoacetates of the formula (III) are generally known compounds in organic chemistry.

Formula (V) provides a general definition of p-toluenesulphonylmethyl isocyanide (TOSMIC) which is furthermore required as a starting compound for carrying out the process according to the invention. p-Toluenesulphonylmethyl isocyanide (TOSMIC) of the formula (V) is known (cf., for example, Synthesis 1985, 400-402; J. Org. Chem. 42, 1153-1159 [1977]; Tetrahedron Lett. 1972, 2367-2368).

The α-cyano-cinnamates of the formula (IV) which are formed as intermediates when the process according to the invention is carried out are hitherto unknown and are also a subject of the invention.

Suitable diluents for carrying out the first and second step of the process according to the invention are inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform or carbon tetrachloride; ethers such as diethyl ether, diisopropyl ether, dioxane, tetrahydrofuran or ethylene glycol dimethyl ether or ethylene glycol diethyl ether; ketones such as acetone or butanone or methyl isobutyl ketone; nitriles such as acetonitrile, propionitrile or benzonitrile; amides such as N,N-dimethylformamide, N,N-dimethylacetamide, N-methylformanilide, N-methylpyrrolidone or hexamethyl phosphoric triamide, esters such as methyl acetate or ethyl acetate, or sulphoxides such as dimethyl sulphoxide.

Step 1 of the process according to the invention is preferably carried out in the presence of a suitable reaction auxiliary. Reaction auxiliaries which are suitable are all customary inorganic or organic acids or bases. These include, for example, alkaline earth metal hydroxides or alkali metal hydroxides such as sodium hydroxide, calcium hydroxide, potassium hydroxide, but also ammonium hydroxide, alkali metal carbonates such as sodium carbonate, potassium carbonate, potassium hydrogen carbonate, sodium hydrogen carbonate or ammonium carbonate, alkali metal acetates or alkaline earth metal acetates such as sodium acetate, potassium acetate, calcium acetate or ammonium acetate, and also tertiary amines such as trimethylamine, triethylamine, tributylamine, N,N-dimethylaniline, pyridine, piperidine, N-methylpiperidine, N,N-dimethylaminopyridine, diazabicyclooctane (DABCO), diazabicyclononene (DBN) or diazabicycloundecene (DBU), but also acids such as, for example, p-toluenesulphonic acid.

When carrying out the first step of the process according to the invention, the reaction temperatures can be varied within a substantial range. In general, the process is carried out at temperatures between 0° C. and 160° C., preferably at temperatures between 20° C. and 120° C.

The first step of the process according to the invention is customarily carried out under atmospheric pressure. However, it is also possible to carry out the process under increased or reduced pressure.

For carrying out the first step of the process according to the invention, 1.0 to 5.0 moles, preferably 1.0 to 1.5 moles, of alkyl cyanoacetate of the formula (III) and, if appropriate, 1.0 to 5.0 moles, preferably 1.0 to 2.5 moles, of reaction auxiliary are generally employed per mole of 2-chloro-3-trifluoromethylbenzaldehyde of the formula (II).

The reaction is carried out and the reaction products are worked up and isolated by generally customary methods (in this context, c.f., for example JP 58116462 or the Preparation Examples).

The second step of the process according to the invention is preferably carried out in the presence of a suitable reaction auxiliary. Reaction auxiliaries which are suitable are all inorganic and organic bases which can customarily be used. The following are preferably used: alkali metal hydrides, hydroxides, amides, alcoholates, carbonates or hydrogen carbonates such as, for example, sodium hydride, sodium amide, sodium hydroxide, sodium methylate, sodium ethylate, potassium t-butylate, sodium carbonate or sodium hydrogen carbonate, but also tertiary amines such as, for example, triethylamine, N,N-dimethylaniline, pyridine, N,N-dimethylaminopyridine, diazabicyclooctane (DABCO), diazabicyclononene (DBN) or diazabicycloundecene (DBU).

When carrying out the second step of the process according to the invention, the reaction temperatures can be varied within a substantial range. In general, the process is carried out at temperatures between −30° C. and +40° C., preferably at temperatures between −20° C. and +20° C.

The second step of the process according to the invention is customarily carried out under atmospheric pressure. However, it can also be carried out under increased or reduced pressure.

For carrying out the second step of the process according to the invention, 1.0 to 2.0 moles, preferably 1.0 to 1.2 moles, of p-toluenesulphonylmethyl isocyanide (TOSMIC) of the formula (V) and, if appropriate, 1.0 to 2.0 moles, preferably 1.0 to 1.2 moles, of base used as reaction auxiliary are generally employed per mole of α-cyano-cinnamate of the formula (IV). The reaction is carried out and the reaction products are worked up and isolated by generally customary methods (in this context, cf., for example, JP 58116462 or the Preparation Examples).

The active compounds according to the invention have a powerful action against pests and can be employed in practice for combating undesired harmful organisms. The active compounds are suitable, for example, for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, *Pythium ultimum*; Phytophthora species, such as, for example, *Phytophthora infestans*; Pseudoperonospora species, such as, for example, *Pseudoperonospora humuli* or *Pseudoperonospora cubensis*; Plasmopara species, such as, for example, *Plasmopara viticola*; Peronospora species, such as, for example, *Peronospora pisi* or *Peronospora brassicae*; Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *Pyrenophora graminea* (conidia form: Drechslera, synonym: Helminthosporium); Cochliobolus species, such as, for example, *Cochliobolus sativus* (conidia form: Drechslera, synonym: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae*; Pseudocercosporella species, such as, for example, *Pseudocercosporella herpotrichoides*. The good toleration, by plants, of the active compounds, at the concentrations required for combating plant diseases, permits treatment of above-ground parts of plants, of vegetative propagation stock and seeds, and of the soil.

In this context, the active compounds according to the invention can be employed with particularly good success for combating cereal diseases such as, for example, against the causative organism of powdery mildew of cereals (*Erysiphe graminis*) or against the causative organism of snow mould of cereals (*Fusarium nivale*) or for combating diseases in fruit and vegetable growing, such as, for example, against the causative organism of grey mould on beans (*Botrytis cinerea*) or for combating rice diseases such as, for example, against the causative organism of rice blast disease (*Pyricularia oryzae*). Besides, the active compounds according to the invention have a broad in-vitro activity. Moreover, the active compounds according to the invention also show a leaf-acting insecticidal activity when used at appropriate dosage rates.

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and in mixtures with fertilisers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomising, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range: They lie, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

Besides the abovementioned activity against phytopathogenic microorganisms, the active compounds according to the invention are distinguished by a broad and powerful microbicidal action against a broad range of microorganisms which are relevant to the protection of materials, and by a noticeably good activity against algae and slime organisms. The substances according to the invention are therefore outstandingly suitable for the protection of industrial materials.

Industrial materials in this context are understood as meaning non-live materials which have been prepared for use in industry. For example, industrial materials which are intended to be protected by active compounds according to the invention from microbial change or destruction can be glues, sizes, paper and board, textiles, leather, wood, paints and plastic articles, cooling lubricants and other materials which can be infested with, or destroyed by, microorganisms. Parts of production plants, for example cooling-water circuits, which may be impaired by the multiplication of microorganisms may also be mentioned within the scope of the materials to be protected. Industrial materials which may be mentioned within the scope of the present invention are preferably glues, sizes, papers and boards, leather, wood, paints, plastic articles, cooling lubricants and cooling circuits.

Microorganisms, capable of bringing about degradation of, or change in, the industrial materials, which may be mentioned are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae.

Microorganisms of the following genera may be mentioned as examples:

Alternaria, such as *Alternaria tenuis;*
Aspergillus, such as *Aspergillus niger;*
Chaetomium, such as *Chaetominum globosum;*
Coniophora, such as *Coniophora puteana;*
Lentinus, such as *Lentinus tigrinus;*
Penicillium, such as *Penicillium glaucum;*
Polyporus, such as *Polyporus versicolor;*
Aureobasidium, such as *Aureobasidium pullulans;*
Sclerophoma, such as *Sclerophoma pityophila;*
Trichoderma, such as *Trichoderma viride;*
Escherichia, such as *Escherichia coli;*
Pseudomonas, such as *Pseudomonas aeruginosa;*
Staphylococcus, such as *Staphylococcus aureus.*

Depending on the field of application, an active compound according to the invention can be converted into the customary formulations such as solutions, emulsions, suspensions, powders, pastes or granules.

These can be prepared in a manner known per se, for example by mixing the active compounds with an extender consisting of liquid solvent and/or solid carriers, optionally with the use of surface-active agents such as emulsifiers and/or dispersing agents, it being possible, if appropriate, for organic solvents such as alcohols to be used as auxiliary solvents if water is used as the extender. Examples of liquid solvents for the active compounds can be water, alcohols, preferably ethanol or isopropanol or benzyl alcohol, ketones such as acetone or methyl ethyl ketone, liquid hydrocarbons such as benzine fractions, halogenated hydrocarbons such as 1,2-dichloroethane.

Microbicidal agents contain the active compounds, in general, in an amount of from 1 to 95%, preferably from 10 to 75%.

The use concentrations of active compounds according to the invention depend on the nature and the occurrence of the microorganisms to be combated and on the composition of the material to be protected. The optimum dosage rate can be determined by test series. In general, the use concentrations are in the range from 0.001 to 5% by weight, preferably from 0.05 to 1.0% by weight, relative to the material to be protected.

The active compounds according to the invention can also be used as a mixture with other known active compounds. Examples of active compounds which may be mentioned are the following: benzyl alcohol mono- (or poly)hemiformal and other formaldehyde-releasing compounds, benzimidazolylmethylcarbamates, tetramethyldiuram disulphide, zinc salts of dialkyldithiocarbamates, 2,4,5,6-tetrachloroisophthalonitrile, thiazolylbenzimidazole, mercaptobenzothiazole, organotin compounds, methylene bisthiocyanate, phenol derivatives such as 2-phenylphenol, (2,2'-dihydroxy-5,5'-dichloro)-diphenylmethane, 3-methyl-4-chlorophenol, 2-thiocyanatomethylthiobenzthiazole, N-trihalogenomethylthio compounds such as folpet, fluorfolpet and dichlofluanid, azole fungicides such as triadimefon, triadimenol, bitertanol, tebuconazole, propiconazole, azoconazole, iodopropargyl derivatives such as iodopropargyl butylcarbamate and iodopropargyl phenylcarbamate, isothiazolinone compounds such as kathon, and also quaternary ammonium compounds such as benzalkonium chloride.

Mixtures of the substances to be used according to the invention with known insecticides can also be used. Examples which may be mentioned here are: organophosphorus compounds such as chlorpyriphos or phoxim, carbamates such as aldicarb, carbosulfan or propoxur, or pyrethroids, such as permethrin, cyfluthrin, cypermethrin, deltamethrin or fenvalerate.

Other suitable components for mixtures are algicides, molluscicides as well as active substances against "sea animals" which populate ship's bottom paints.

PREPARATION EXAMPLES

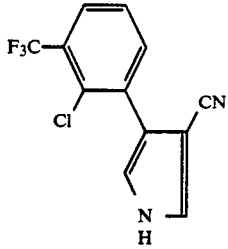

To 34.8 g (0.115 mol) of ethyl 2-cyano-3-(2-chloro-3-trifluoromethylphenyl)-acrylate in 80 ml of dry ethanol there are added dropwise with stirring at 0° C. to 5° C. a solution of 3.5 g (0.154 mol) of sodium in 80 ml of ethanol and subsequently also dropwise with stirring at 0° C. to 5° C. a solution of 23.6 g (0.121 mol) of p-toluenesulphonylmethyl isocyanide (TOSMIC) in 120 ml of dry dichloromethane. When the addition is complete, stirring is continued for one hour at 0° C. and for 16 hours at room temperature, the pH of the reaction mixture is then brought to pH 8 using 2N hydrochloric acid, the organic phase is separated off, dried over sodium sulphate and concentrated in vacuo, the residue is taken up in dichloromethane, and the mixture is washed with water, dried over sodium sulphate, concentrated in vacuo, and volatile components are removed under a high vacuum. The crystalline residue is dried by pressing on clay.

26.3 g (85 % of theory) of 3-(2-chloro-3-trifluoromethylphenyl)-4-cyanopyrrole of melting point 82° C. are obtained.

PREPARATION OF THE STARTING COMPOUND:

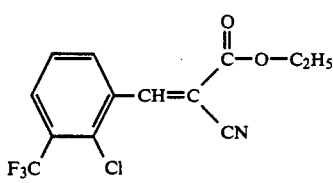

To 31.0 g (0.149 mol) of 2-chloro-3-trifluoromethylbenzaldehyde (cf., for example, EP 145,334) and 18.5 g (0.164 mol) of ethyl cyanoacetate in 75 ml of toluene there is added dropwise with stirring a solution of 1 ml of piperidine in 5 ml of toluene, during which process the temperature of the reaction mixture rises to approx. 40° C. When the addition is complete, the mixture is stirred for 2 hours at 70° C., then cooled to room temperature, washed three times with water and dried over sodium sulphate, and the solvent is removed in vacuo.

37.3 g (83% of theory) of ethyl 2-cyano-3-(2-chloro-3-trifluoromethylphenyl)-acrylate of melting point 50° C. are obtained.

USE EXAMPLES

In the Use Examples which follow, the compound shown below was employed as comparison substance:

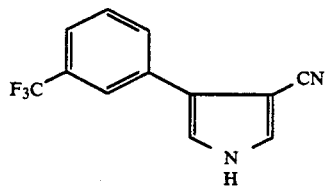

3-(3-trifluoromethylphenyl)-4-cyanopyrrole (disclosed in EP 96,142).

EXAMPLE A

Erysiphe Test (Wheat)/Protective

Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. tritici.

The plants are placed in a greenhouse at a temperature of about 20° C. and a relative atmospheric humidity of about 80%, in order to promote the development of powdery mildew pustules.

Evaluation is carried out 7 days after the inoculation.

A clearly superior activity compared with the prior art is shown, in this test, by the compound according to the invention.

EXAMPLE B

*Fusarium nivale* test (Rye) / Seed Treatment

The active compounds are used in the form of dry-dressing agents. They are prepared by extending the active compound in question with powdered rock to give a finelypulverulent mixture which allows uniform distribution on the seed surface.

To dress the seed, the infected seed together with the seed-dressing agent is shaken for 3 minutes in a closed glass flask.

Rye is sown in standard soil at a depth of 1 cm, using 2 batches of 100 grains, and grown in the greenhouse at a temperature of about 10° C. and a relative atmospheric humidity of about 95 % in seed boxes which are exposed to the light for 15 hours per day.

The plants are evaluated for snow mould symptoms about 3 weeks after sowing.

A clearly superior activity compared with the prior art is shown, in this test, by the compound according to the invention.

EXAMPLE C

Botrytis Test (Dwarf Bean) / Protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the active compound preparation until dripping wet. After Ex. A the spray coating has dried on, 2 small agar pieces covered with Botrytis cinerea are placed on each leaf. The inoculated plants are placed in a darkened, humid chamber at 20° C. The size of lesions on the leaves is evaluated 3 days after inoculation.

The size of lesions on the leaves is evaluated 3 days after inoculation.

A clearly superior activity compared with the prior art is shown, in this test, by the compound according to the invention.

We claim:

1. 3-(2-Chloro-3-trifluoromethylphenyl)-4-cyanopyrrole of the formula

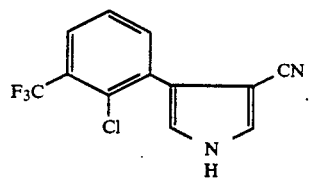

2. A fungicidal composition comprising a fungicidally effective amount of the compound according to claim 1 and an inert diluent.

3. A method of combating fungi which comprises applying to such fungi or to a fungus habitat a fungicidally effective amount of the compound according to claim 1.